United States Patent [19]

Hakim et al.

[11] 4,106,510

[45] Aug. 15, 1978

[54] SERVO VALVE

[75] Inventors: Salomon Hakim; Carlos A. Hakim, both of Bogota, Colombia

[73] Assignee: Hakim Company Limited, Saint Vincent, Saint Vincent

[21] Appl. No.: 745,072

[22] Filed: Nov. 26, 1976

[51] Int. Cl.² .............................................. A61M 27/00
[52] U.S. Cl. .................................. 128/350 V; 128/274; 137/494; 137/505.15
[58] Field of Search ..................... 128/1 R, 274, 350 V; 137/494, 505.15

[56] References Cited

U.S. PATENT DOCUMENTS

| 1,935,548 | 11/1933 | Eggleston et al. | 137/494 |
| 3,276,470 | 10/1966 | Griffing | 137/505.15 |
| 3,586,082 | 6/1971 | Muller | 137/494 |
| 3,886,948 | 6/1975 | Hakim | 128/350 V |

Primary Examiner—Dalton L. Truluck
Attorney, Agent, or Firm—Kenway & Jenney

[57] ABSTRACT

The servo valve disclosed herein is rendered essentially insensitive to changes in pressure across the valving element by providing spring biasing of the valving element which is controlled by a diaphragm exposed to the inlet and outlet pressures. In a particular embodiment, the diaphragm is spring biased and the spring rates for the diaphragm and the valve element are selected in such proportion that the change in biasing force on the valve element exactly compensates for any change in inlet pressure. Therefore, the valve remains closed for any inlet pressure, unless the bias on the spring rates is unbalanced by a signal coming from a sensor.

9 Claims, 4 Drawing Figures

SERVO VALVE

BACKGROUND OF THE INVENTION

The present invention relates to a precision servo valve and more particularly to a hydraulic servo system for treating hydrocephalus.

The treatment of hydrocephalus by means of a servo valve system has been previously described. See, for example, Hakim U.S. Pat. Nos. 3,886,948 and 3,924,635. The servo valve of the present invention was conceived as an improvement over the various servo valves disclosed in those patents. The advantages of the present servo valve, however, will be useful in servo systems generally and particularly in servo systems where very small pressures and volumes are involved since, in almost all servo systems, it is desirable to increase the loop gain and reduce the sensitivity of the system to extraneous variables, advantages which are provided by the construction of the present invention.

With regard to servo valves generally and, in particular, a servo valve intended for use in a hydrocephalus shunt system, it is highly desirable that the valve be very sensitive to the control parameter and relatively insensitive to any other variable, particularly inlet and outlet pressures. While there are certain types of valves that are inherently insensitive to inlet and outlet pressures, e.g. gate valves, ball valves, and the like, they are of relatively complicated construction and typically introduce a substantial element of friction into the system, destroying the accuracy of the servo operation and making it much less sensitive to the control parameter.

For a hydraulic system such as a hydrocephalus shunt servo system, which has to be miniaturized and which must work at relatively low pressures and volumes, the greatly preferred forms of valves are simple check valves in which a valve element works against a valve seat to control flow through the valve, i.e. from the inlet and the outlet. Such valves can be made very reliable, can be highly miniaturized, and further tend to be self-cleaning. Typically, however, such valves are inherently responsive to the pressure differential across the valve, i.e. they are responsive to both inlet pressure and outlet pressure. Indeed, when operated as simple check valves, they are necesarily so. When such valves are then utilized in servo systems, the servo loop must have sufficient gain so that the control variable effects and dominates operation of the opening and closing of the valve in spite of some responsiveness of the valve to inlet and outlet pressures. Thus, if the control signal cannot be made very large, an effort must be made to reduce the operative cross-sectional area of the valve element itself so as to reduce the effect of upstream and downstream pressures. In a system which is already miniaturized, such as a hydrocephalus shunt system, this further complicates the design. The present invention, by reducing sensitivity to undesired variables and mantaining a balance which can be easily controlled by an appropriately applied imbalancing force, allows a small control signal to control relatively large pressures and volumes, even though absolute values are small. In other words, high sensitivity is provided.

Among the several objects of the present invention may be noted the provision of a servo valve which is essentially insensitive to variations in inlet and outlet pressures; the provision of such a valve which is highly reliable; the provision of such a valve in which the valving elements are of relatively simple, check valve type of construction; the provision of such a servo valve which is highly sensitive to the control parameter; the provision of such a valve which is operable at relatively low pressures and relatively low flow volumes and which is therefore suitable for employment in a hydrocephalus shunt system; and the provision of such a valve which is of relatively simple and inexpensive construction. Other objects and features will be in part apparent and in part pointed out hereinafter.

BRIEF DESCRIPTION OF THE INVENTION

A servo valve in accordance with the present invention employs a valve element and a valve seat against which the valve element operates to control flow through the valve. A first spring means is provided for biasing the valve element toward the seat in a manner tending to close the valve. A diaphragm is utilized for pressure sensing, one side of the diaphragm being exposed to the valve inlet pressure. Second spring means are provided for biasing the diaphragm against the inlet pressure. In accordance with the invention, the bias exerted by the first spring means is controlled as a function of diaphragm displacement in a manner tending to increase the bias as the inlet pressure increases. Accordingly, the sensitivity of the valve itself to inlet pressure variations is reduced.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
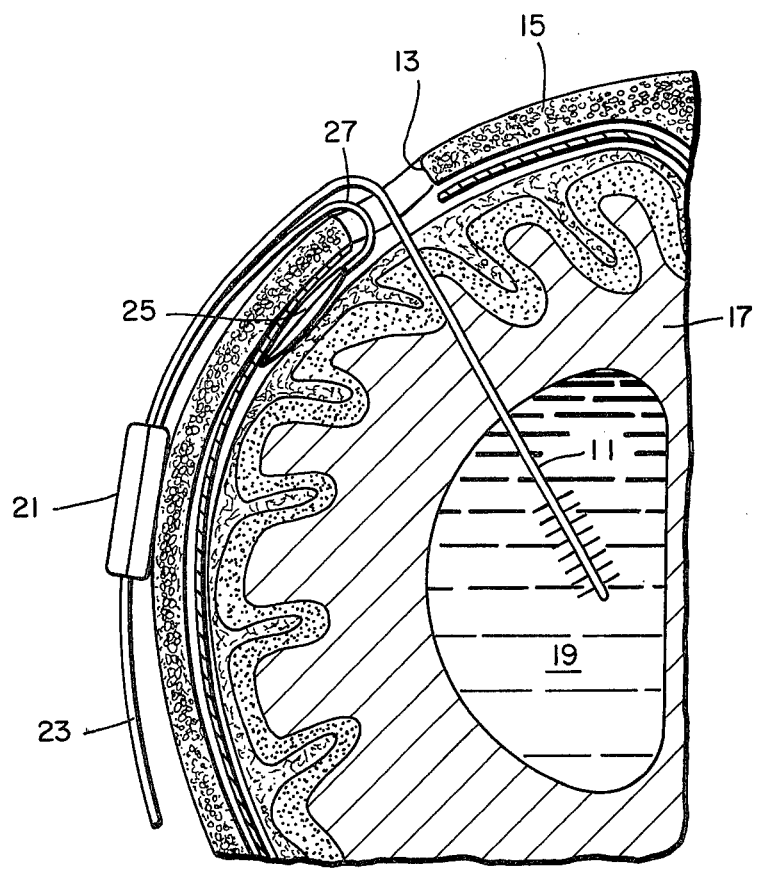
FIG. 1 illustrates a hydrocephalus treatment system employing a servo valve in accordance with the present invention and shows the application of the system to a patient, portions of the patient's head being shown in section.

The implantation of a ventricular shunt system as may employ a servo valve in accordance with the present invention is illustrated in FIG. 1. A ventricular catheter 11 is inserted through a burr hole 13 in the patient's skull 15 and thence through the brain tissue 17 into the ventricle 19. The ventricular catheter is connected, through a servo valve 21, to a drainage catheter 23. The drainage catheter will normally lead to the right atrium, the peritoneal cavity, or some other suitable drain situs. The shunt path established by this connection permits cerebro-ventricular fluid (CSF) to drain from the ventricle 19 so as to relieve the symptoms of hydrocephalus. In accordance with the teachings in the U.S. Pat. No. 3,886,948 patent, identified previously, the drainage of the ventricle should not be completely free nor merely limited by some preselected back pressure. Rather, flow from the ventricle is preferably controlled in a dynamic fashion in response to the force exerted on a sensor, indicated at 25, which is implanted in the sub-dural space.

One method of fabricating such a sensor is described in U.S. Pat. No. 3,958,562 entitled Implantable Pressure Sensor and issued to Salomon Hakim and Don Harris on May 25, 1976. The sensor is filled with an appropriate hydraulic fluid, i.e. a liquid, and communicates with the servo valve through a flexible conduit 27.

The force detected by sensor 25 acts as the control parameter for selectively opening the valve so as to permit drainage of CSF from the ventricle 19. An analysis of the forces acting upon the brain as the result of varying pressures within the ventricle, particularly in the face of changing ventricular size, is presented in an article appearing in the March, 1976 issue of *Surgical Neurology, Volume* 5, entitled "The Physics of the Cranial Cavity, Hydrocephalus and Normal Pressure Hydrocephalus: Mechanical Interpretation and Mathematical Model" by Solomon Hakim, Jose Gabriel Venegas, and John D. Burton. Among other matters, this article explores the rationale of considering sub-dural stress as the preferred indicator of ventricular condition rather than utilizing a mere measurement of hydraulic pressure within the ventricle.

The principle of operation of the servo valve of the present invention may be most easily explained with reference to FIG. 2. In the servo valve illustrated diagrammatically in FIG. 2, the valving element is merely a simple spherical ball 31 which works against a conical seat 33. Ball 31 is biased against seat 33 by a spring 35, the other end of which rests against a lever 37 which can rock around a pivot point, indicated at 39. An inlet conduit 41 communicates with both the valve seat 33 and a pressure sensing diaphragm 43.

Diaphragm 43 comprises a relatively stiff central disk portion 45 and a limp annular suspension 47. The operative area of the diaphragm is designated A1 for reference is subsequent analysis. As well as working upon the diaphragm 43, it will be understood that the inlet pressure also operates against the valve ball 32, i.e. an increasing inlet pressure tends to open the valve by pushing against the portion of the surface of the ball 31 which is exposed through the seat 33. The effective area against which this pressure can work is designated A2 for use in subsequent analysis.

The diaphragm 43 is mechanically connected to a link 49 to the end of lever 37 opposite the valve ball 31. A spring 51 applies to the diaphragm 43 a biasing force which opposes the inlet pressure. The spring constant or rate of the springs against which the diaphragm works is designated K1. In this embodiment, the diaphragm 43 must compress both of the springs 35 and 51 and thus K1 is the sum of the spring constants of the two springs, referenced to the diaphragm and considering any mechanical advantage which may be provided by the lever 37. The spring constant K1 thus determines the compliance of the diaphragm 43, i.e. the extent to which it will be displaced upwardly by increasing inlet pressures. As the diaphragm 43 is displaced upwardly by increasing inlet pressures, it can be seen that, through the lever 37, this movement will vary or control the bias force exerted by the spring 35 on the valving element 31. The inherent rate for the spring 35 is designated K2 for use in subsequent analysis. It should be understood that this is the spring rate which would be applicable for movement of the valve ball 31 alone, all other elements of the system being restrained.

If the spring rates and the lengths of the lever arms are appropriately chosen, the adjustment of the biasing force applied by the spring 35 can balance, essentially exactly, the variation in opening force exerted on the valving element itself by a changing inlet pressure so that the operation of the valve becomes essentially independent of inlet pressure. In this way, the valve can be rendered highly sensitive to the control parameter alone. To establish this desirable situation, the relationship should be such that $(K1/K2) = R \times (A1/A2)$, where $R$ is the ratio of the lengths of the two arms of the lever 37. In the embodiment illustrated, this ratio is assumed to be unity so that the relationship reduces to $(K1/K2) = (A1/A2)$.

The control force which then actually controls the opening and closing of the valve may be applied in any convenient manner, e.g. by a pushrod or torque rod coupled to the lever or to the diaphragm 43. However, in the embodiment illustrated in FIG. 2, the outlet chamber 42 is sealed off from the back side of the diaphragm 43 so that a control force in the form of a hydraulic pressure may be coupled to a chamber 44 which is on the opposite side of the diaphragm 43 from the inlet chamber 40. Accordingly, though the valving element will not be displaced by variations in inlet pressure, any charge in the control pressure will upset the balance and allow the valve to operate.

Figure 2:
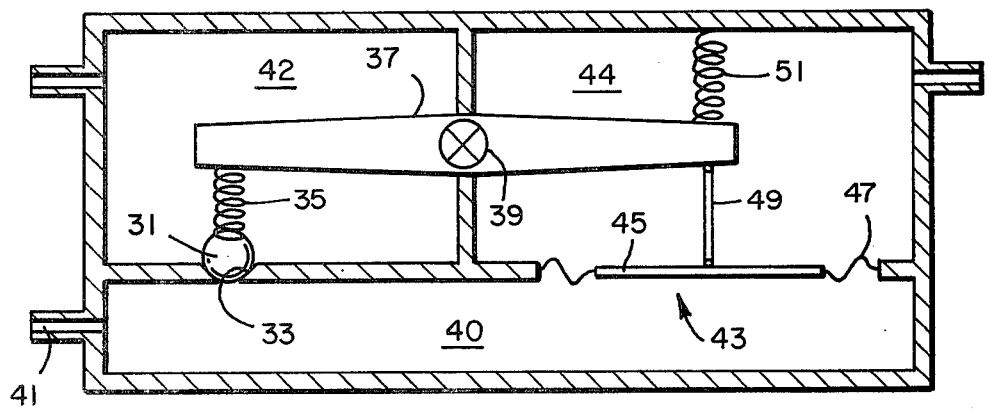
FIG. 2 is a diagrammatic illustration of a valve in accordance with the present invention, useful for illustrating certain operating relationships.

While the arrangement illustrated in FIG. 2 can be rendered essentially insensitive to variations in inlet pressure, variations in outlet pressure can still somewhat affect the operation of the valve since these variations in pressure can also work upon the effective area A2 of the valving element. Essential insensitivity to both inlet and outlet pressures can be provided if the back side of the sensing diaphragm is exposed to the outlet pressure. While the arrangement of FIG. 2 could be modified to provide this aspect, this feature can be provided in an especially simple construction if the valve seat is carried upon the sensing diaphragm itself. With such an arrangement, the pressures operating on the two sides of the diaphragm are, by definition, clearly identical to the pressures operating on the two sides of the effective area of the valving element. A presently preferred form of such a valve, suitable for use in a hydrocephalus shunt system, is illustrated in FIG. 3.

Figure 3:
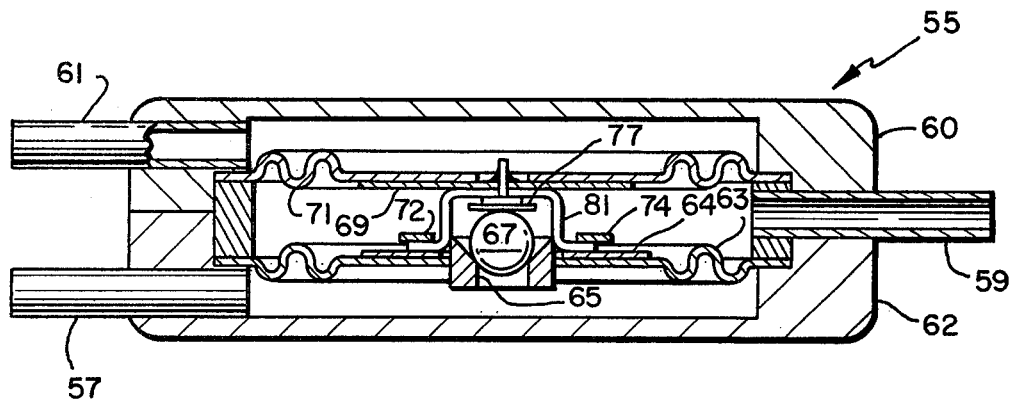
FIG. 3 is a side view, with parts broken away, of another form of servo valve constructed in accordance with the present invention.

Referring to FIG. 3, a generally disk-like valve body 55 is provided with lateral openings for receiving a tubular inlet stem 57, tubular outlet stem 59, and a tubular stem 61 for communicating a hydraulic control pressure. The valve body is conveniently constructed of a suitable plastic in two halves 60 and 62. The valve comprises both an upper and a lower diaphragm. The lower diaphragm corresponds to the sensing diaphragm 43 of FIG. 2 and comprises a metal, disk-like central portion 64, and a limp, annular surround 63, e.g. constructed of silicone rubber. The disk 64 includes the valve seat 65 against which a spherical valving element 67 can operate.

The upper diaphragm is generally similar to the lower diaphragm, comprising a rigid disk 69 and a limp surround or suspension 71, the essential difference being that the disk 69 is solid rather than including a valve seat. The two diaphragms are linked so as to move by a stirrup-like element 81. The wide lower portion of the stirrup-like element 81 straddles the valve seat 65 and is welded to the diaphragm disk 64 while the narrow upper or stem portion of the stirrup-like element 81 passes through a hole in the other diaphragm disk 69 where it is cemented in place in final assembly.

Figure 4:
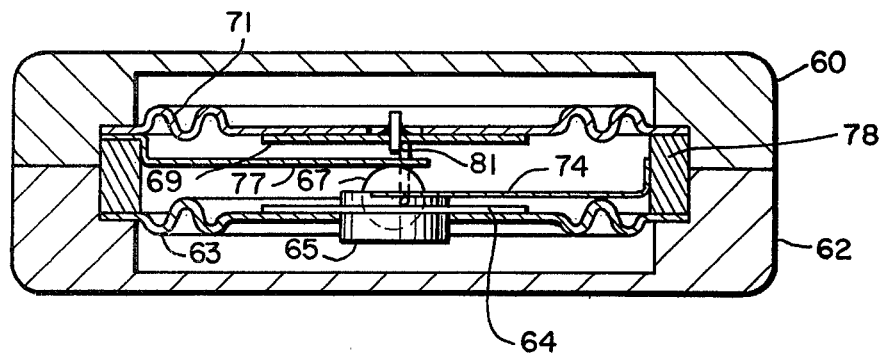
FIG. 4 is a side view of the valve of FIG. 3, turned 90° to show the arrangement of springs therein.

The lower diaphragm is biased against the inlet pressure by a pair of leaf springs 72 and 74. These springs correspond in function to the spring 51 of the arrangement shown in FIG. 2. The spherical valving element 67 is biased towards the seat 65 by a leaf spring 77 which corresponds in function to the spring 35 of the arrangement of FIG. 2. The springs are attached to a metal ring 78 which is clamped between the two body halves 60 and 62, as shown in FIG. 4.

In the embodiment of FIG. 3, movement of the inlet pressure sensing diaphragm 64 affects the biasing force applied to the valving element by displacing the whole valve towards the spring 77 rather than moving the spring with respect to the valve assembly as in the previous embodiment. The effect, however, is the same. Thus, by appropriately choosing the spring constants of the springs 72 and 74 in relation to the spring constant of the spring 77, the operation of the valve can be rendered essentially independent of inlet pressure. Further, since the outlet pressure is applied to the opposite side of the diaphragm 64 as well as to the back side of the spherical valving element 67, it can be seen that the operation of the valve will also be essentially independent of outlet pressure. In this embodiment, the value for R is inherently equal to 1 since movement of the diaphragm 64 directly translates the valving member 67 against its biasing spring 77. In this embodiment also, the interpretation of K1 as including components from one or both of the spring sets will of course depend upon whether the effective area of the diaphragm includes the area of the valve seat. Notwithstanding the form of analysis, the operation is, in effect, to provide a parallel compliance of the diaphragm and the valving element so that increasing inlet pressures do not tend to lift the valving element off its seat. This balance is, however, easily upset by a control force so that the actual opening of the valve remains very sensitive to the control parameter.

In the FIG. 3 embodiment, a control pressure applied to the top surface of the diaphragm 69 will exert a force downwardly, through the stirrup-like element 81 and against the diaphragm 64, thus affecting the balance just described. Accordingly, the valve will operate as a function of the control pressure. In this embodiment, the control pressure operates relative to outlet pressure although it should be understood that other means of applying the control force can also be arranged, e.g. in which a control force is mechanically applied or is applied as a pressure working against some other pressure, e.g. atmospheric. Myriad other variations for applying the control signal will be apparent to those skilled in the art but do not affect the essential operation in accordance with the present invention, i.e. the ability to render the operation of the valve essentially insensitive to inlet pressure, outlet pressure, or both.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

We claim:

1. A servo valve comprising:
    a valve element;
    a valve seat against which said valve element operates to control flow through the valve, the inlet pressure tending to open the valve;
    first spring means for biasing said valve element in a manner tending to close the valve;
    a diaphragm one side of which is exposed to the inlet pressure;
    second spring means biasing said diaphragm against the inlet pressure thereby defining the compliance of the diaphragm to changes in inlet pressure;
    said diaphragm, said valve element and said seat being mechanically coupled in such a manner that the bias exerted by said first spring means is responsive to displacement of said diaphragm in such a manner that the force exerted by said first spring means on said valve element is increased in the same proportion as any increase in the inlet pressure so that the valve remains closed in the absence of any unbalancing additional force; and
    means for applying to said valve element an additional, control force for controlling its opening whereby the opening of said valve is responsive to said control force but is essentially insensitive to changes in inlet pressure.

2. A servo valve as set forth in claim 1 wherein said diaphragm is coupled to said first spring means through by a lever for varying the bias applied by said spring to said valve element as a function of diaphragm displacement.

3. A servo valve comprising:
    a valve element;
    a valve seat against which said valve element operates to control flow through the valve, the inlet pressure tending to open the valve;
    first spring means for biasing said valve element in a manner tending to close the valve;
    a diaphragm one side of which is exposed to the inlet pressure;
    a second spring means biasing said diaphragm against the inlet pressure thereby defining the compliance of the diaphragm to changes in inlet pressure, said seat being carried by said diaphragm so that displacement of said diaphragm by increasing inlet pressure directly displaces said seat and said valve element against said first spring means for increasing the bias force applied to said valve element, said diaphragm, said valve element and said seat being thereby mechanically coupled in such a manner that the bias exerted by said first spring means is responsive to displacement of said diaphragm whereby the sensitivity of the valve opening to inlet pressure is reduced.

4. A servo valve comprising:
    a valve element;
    a valve seat against which said valve element operates to control flow through the valve, said valve element presenting to the inlet pressure an area A2 against which the inlet pressure operates tending to open the valve;
    first spring means for biasing said valve element in a manner tending to close the valve, said first spring means having a spring factor K2 for movement of said valve element alone with respect to said seat;
    a diaphragm having an effective area A1, one side of which is exposed to the inlet pressure;
    further spring means biasing said diaphragm against the inlet pressure to provide a spring factor K1 defining the compliance of the diaphragm to changes in inlet pressure;

means responsive to displacement of said diaphragm for varying the bias exerted by said first spring means between said valve element and said valve seat in proportion, by a factor R, to the diaphragm displacement such that $$(K1/K2) = (A1/A2)$$

whereby the valve opening is essentially insensitive to inlet pressure; and means for applying to said valve element an additional, control force for controlling its opening whereby the opening of said valve is responsive to said control force but is essentially insensitive to changes in inlet pressure.

5. A servo valve as set forth in claim 4 wherein $R = 1$.

6. A servo valve comprising:

a valve element;

a diaphragm having an effective area A1, one side of which is exposed to the inlet pressure, the diaphragm being apertured to provide a valve seat against which said valve element operates to control flow through the valve, said valve element presenting to the inlet pressure an area A2 against which the inlet pressure operates tending to open the valve;

first spring means for biasing said valve element in a manner tending to close the valve, said first spring means having a spring factor K2 for movement of said valve element alone with respect to said seat;

further spring means biasing said diaphragm against the inlet pressure to provide a spring factor K1 defining the compliance of the diaphragm to changes in inlet pressure, the value of K1 being such that $$(K1/K2) = (A1/A2)$$

whereby the valve opening is essentially insensitive to pressure differential across the valve.

7. A servo valve as set forth in claim 6 further comprising a second diaphragm for responding to a control pressure, said second diaphragm being coupled to said first diaphragm for applying a control force thereto to effect opening of said valve.

8. A servo valve as set forth in claim 7 wherein said second diaphragm is back to back with said first diaphragm and both have one side exposed to the valve outlet pressure.

9. A cerebro-ventricular shunt system comprising:

a ventricular catheter adapted for implantation to release CSF from a patient's ventricle;

a drainage catheter;

a servo valve connecting said ventricular and drain catheters, said valve including:

a valve element;

a valve seat against which said valve element operates to control flow through the valve, said valve element presenting to the inlet pressure an area A2 against which the inlet pressure operates tending to open the valve;

first spring means for biasing said valve element in a manner tending to close the valve, said first spring means having a spring factor K2 for movement of said valve element alone with respect to said seat;

a diaphragm having an effective area A1, one side of which is exposed to the inlet pressure;

further spring means biasing said diaphragm against the inlet pressure to provide a spring factor K1 defining the compliance of the diaphragm to changes in inlet pressure;

said diaphragm, said valve element, and said seat being mechanically interconnected in such manner that the bias exerted by said first spring means is responsive to displacement of said diaphragm by a factor R, such that $$(K1/K2) = (A1/A2)$$

thereby to render the valve opening essentially insensitive to inlet pressure; and pressure sensing means for applying to said diaphragm a force corresponding to subdural stress.

* * * * *

UNITED STATES PATENT AND TRADEMARK OFFICE
CERTIFICATE OF CORRECTION

PATENT NO. : 4,106,510
DATED : August 15, 1978
INVENTOR(S) : Salomon Hakim and Carlos A. Hakim It is certified that error appears in the above-identified patent and that said Letters Patent are hereby corrected as shown below:

On front page of patent, Assignee's address is incorrect. Change "Saint Vincent, Saint Vincent" to --Saint Vincent, British West Indies--;

Column 3, line 38, "valve ball 32" should be --valve ball 31--; line 44, after "connected" but before "a", "to" should be --by--;

Column 7, claim 4, equation on lines 8-10, "$\frac{K1}{K2} = \frac{A1}{A2}$" should be-- $\frac{K1}{K2} = R\frac{A1}{A2}$ --;

Column 8, claim 9, equation on lines 37-39, "$\frac{K1}{K2} = \frac{A1}{A2}$" should be --$\frac{K1}{K2} = R\frac{A1}{A2}$ --.

Signed and Sealed this

Twenty-fourth Day of April 1979

[SEAL]

Attest:

RUTH C. MASON
*Attesting Officer*

DONALD W. BANNER
*Commissioner of Patents and Trademarks*